United States Patent [19]

Jakobson et al.

[11] Patent Number: 5,130,056
[45] Date of Patent: Jul. 14, 1992

[54] CLEANING AGENT AND PROCESS FOR ITS PREPARATION

[75] Inventors: Gerald Jakobson; Werner Siemanowski, both of Rheinberg; Karl-Heinz Uhlig, Krefeld, all of Fed. Rep. of Germany

[73] Assignee: Deutsche Solvay-Werke GmbH, Solingen, Fed. Rep. of Germany

[21] Appl. No.: 468,208

[22] Filed: Jan. 22, 1990

[30] Foreign Application Priority Data

Jan. 27, 1989 [DE] Fed. Rep. of Germany ....... 3902374

[51] Int. Cl.$^5$ .................. C11D 1/12; C11D 1/755; C11D 17/00
[52] U.S. Cl. .................. 252/551; 252/89.1; 252/549; 252/550; 252/DIG. 1; 252/DIG. 5; 252/DIG. 13
[58] Field of Search ......... 252/89.1, DIG. 1, DIG. 5, 252/DIG. 13, 551, 550, 549

[56] References Cited

U.S. PATENT DOCUMENTS

| 2,527,077 | 10/1950 | Preston | 252/121 |
| 3,917,817 | 11/1975 | Vanlerberghe et al. | 252/DIG. 13 |
| 4,419,344 | 12/1983 | Strasilla et al. | 252/545 |
| 4,454,113 | 6/1984 | Hemler | 252/312 |
| 4,783,282 | 11/1988 | Smid | 252/89.1 |
| 4,847,071 | 7/1989 | Bissett et al. | 252/107 |

FOREIGN PATENT DOCUMENTS 2755052 6/1978 Fed. Rep. of Germany.

OTHER PUBLICATIONS

*McCuthcheon's Emulsifiers and Detergents* 1982, p. 65.

*Primary Examiner*—A. Lionel Clinghamn
*Assistant Examiner*—William S. Parks
*Attorney, Agent, or Firm*—Foley & Lardner

[57] ABSTRACT

The present invention relates to a washing agent, cleansing agent and/or toiletry containing at least one ionic and/or amphoteric surfactant and at least one $C_8$ to $C_{18}$ fatty acid monoester of diglycerol and/or $C_8$ to $C_{18}$ fatty acid diester of tetraglycerol as a constituent of the mixture, 2 to 30% by weight, perferably 10 to 20% by weight, of at least one fatty acid monoester of diglycerol and/or fatty acid diester of tetraglycerol, relative to the total surfactant content (100% by weight), being present in the surfactant mixture. The agent is employed together with certain compositions, in particular with a solvent, additives and the like. The invention also relates to the preparation of the washing agent, cleansing agent and/or toiletry and to its use as a shower preparation, bubble bath preparation, liquid hand cleanser or hair shampoo.

24 Claims, No Drawings

CLEANING AGENT AND PROCESS FOR ITS PREPARATION

BACKGROUND OF THE INVENTION

The present invention relates to a washing agent, cleansing agent and/or toiletry containing at least one non-ionic surfactant consisting of a fatty acid ester and at least one ionic and/or amphoteric surfactant. The invention also relates to the process for the preparation of the washing agent, cleansing agent and/or toiletry and to the use thereof.

German 30 33 929 discloses a toiletry based on an aqueous solution of a mixture of certain betaines and one or more anionic compounds belonging to the group composed of sodium alkyl ether-sulfate, ammonium alkyl ether-sulfate, alkanolamine ether-sulfate or alkanolamine alkylsulfate in which the alkyl group has 8 to 14 carbon atoms and certain weight ratios must be maintained. The composition additionally includes 2 to 35% by weight (relative to the betaine) of a glycerol fatty acid ester having a minimum content of 70% by weight of monoesters in which the fatty acid component contains 8 to 18 carbon atoms.

However, this toiletry exhibits the disadvantages that the fatty acid ester present in the aqueous solution, in particular a glycerol fatty acid monoester, is relatively sparingly soluble in the aqueous solution of the total mixture of surfactants. This is a particular problem when the total surfactant content in the aqueous solution is reduced, so that cloudiness and reduction in activity occur. It is also necessary to melt, and subsequently process, the glycerol fatty acid ester at temperatures above approximately 60° C., or to bring the glycerol fatty acid ester into solution or dispersion by means of a solvent, solubilizer or dispersing agent. Emulsifying and solubilizing properties, such as are preferable, for example, for dissolving perfume oils and/or other active compounds, are only weakly developed in the glycerol fatty acid monoesters.

SUMMARY OF THE INVENTION

It is therefore an object of the present invention to provide a cleaning composition not having the disadvantages of prior compositions.

It is a further object of the invention to improve the effectiveness and/or processability of the agent.

It is yet another object of the invention to provide an agent containing, as a non-ionic surfactant, a chemical compound which meets dermatological and toxicological requirements, in particular one that is well tolerated by the skin and that shows no toxic properties in the concentrations in which it is used. The non-ionic surfactant should be readily biodegradable.

In accordance with these and other objects of the invention, there is provided a washing agent, cleansing agent or toiletry comprising, in admixture, at least one non-ionic fatty acid ester surfactant selected from the group consisting of a $C_8$ to $C_{18}$ fatty acid monoester of diglycerol and a $C_8$ to $C_{18}$ fatty acid diester of tetraglycerol, and at least one ionic or amphoteric surfactant. The agent can be used to clean the human body, in a method comprising the steps of providing an agent as described above, and applying the agent to a portion of the human body to cleanse the body.

Also provided is a process for the preparation of the above-described agent, comprising the steps of reacting a fatty acid alkyl ester having from 8 to 18 carbon atoms in the fatty acid component and from 1 to 4 carbon atoms in the ester component, in an alkaline medium with an isopropylidene derivative of a polyglycerol and a diglycerol or tetraglycerol, at a temperature of 140°–220° C., in vacuo at 950–5 mbar, removing the $C_1$–$C_4$-alcohol thus formed by distillation, purifying the reaction product, hydrolyzing the reaction product by splitting off at least one isopropylidene group at 20° to 100° C., and by acid hydrolysis and mixing the resulting fatty acid monoesters of diglycerol or tetraglycerol at temperatures of 1°–18° C., under a pressure of 0.1 to 1.5 bar, with at least one ionic or amphoteric surfactant.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

It has been found, in accordance with the invention, that a composition containing at least one non-ionic surfactant consisting of a fatty acid ester and at least one ionic and/or amphoteric surfactant provides an improved washing agent, cleansing agent and/or toiletry. The surfactant mixture according to the invention contains at least one $C_8$ to $C_{18}$, preferably $C_9$ to $C_{17}$, fatty acid monoester of diglycerol and/or one $C_8$ to $C_{18}$ fatty acid diester of tetraglycerol as a constituent of the mixture.

In accordance with the invention, the surfactant mixture contains about 2 to 30% by weight, preferably about 10 to 20% by weight, of at least one fatty acid monoester of diglycerol and/or fatty acid diester of tetraglycerol, relative to the total surfactant content (100% by weight). The washing agent, cleansing agent and/or toiletry can be in a solid, liquid (including gel-like or highly viscous form) or pasty form. It is preferable to employ the liquid form.

It was entirely unexpected that the $C_8$ and $C_{18}$ fatty acid monoester of diglycerol and/or the $C_8$ and $C_{18}$ fatty acid diester of tetraglycerol produce the desired results in the surfactant mixture and, inter alia, that this compound would also meet dermatological and toxicological requirements, since diglycerol and tetraglycerol cannot be regarded as homologues of glycerol, and are not trihydric alcohols like glycerol, but are ether-polyalcohols.

The washing agent, cleansing agent and/or toiletry preferably contains, in addition, electrolytes, preferably inorganic chlorides, in amounts by weight of about 0.1 to 8% by weight, preferably about 0.7 to 3% by weight, relative to the total weight of the washing agent, cleansing agent and/or toiletry.

The total surfactant content of the agent, using the surfactant mixture according to the invention, is about 2.5 to 60% by weight, preferably about 7 to 35% by weight. The remainder comprises solvents and/or diluents, preferably water, lower $C_1$ to $C_8$, preferably $C_2$ to $C_4$, alcohols, $C_2$ to $C_8$, preferably $C_3$ to $C_6$, diols and/or glycerol or glycerol derivatives, and at least one electrolyte. The agent may also contain, if appropriate, additives, preferably preservatives, perfumes, dyes, pharmaceutical active compounds, standardizing agents for regulating the pH, complexing agents for masking metal ions and skin preparations and/or thickeners.

In a preferred embodiment, the total surfactant content of the agent is about 2.5 to 60% by weight, preferably about 7 to 35% by weight; the surfactant mixture comprising about 2 to 30% by weight, preferably about 10 to 20% by weight, of at least one $C_{12}$ to $C_{16}$ fatty acid monoester of diglycerol and/or fatty acid diester of tetraglycerol (relative to the total surfactant content, 100% by weight). The agent contains about 7 to 0.1% by weight, preferably about 3 to 0.3% by weight, of at least one electrolyte, preferably composed of or containing sodium chloride, about 90.5 to 39.9% by weight, preferably about 90 to 64.7% by weight, of a solvent and/or diluent, preferably water, lower $C_1$ to $C_8$, preferably $C_2$ to $C_4$, alcohols and/or $C_3$ to $C_8$, preferably $C_3$ to $C_6$, diols. It additionally contains additives in amounts by weight of about 0.005 to 12 parts by weight, preferably about 0.1 to 5 parts by weight (relative to 100 parts by weight of the washing agent, cleansing agent and/or toiletry composed of the surfactant mixture, electrolytes and solvent and/or diluent). These additives preferably comprise preservatives, perfumes, dyes, pharmaceutical active compounds, standardizing agents for regulating the pH, complexing agents for masking metal ions, skin preparations and/or thickeners.

The $C_8$ to $C_{18}$, preferably $C_{12}$ to $C_{16}$, fatty acid monoester of diglycerol and/or the $C_8$ to $C_{18}$, preferably $C_{12}$ to $C_{16}$, fatty acid diester of tetraglycerol produces, in the surfactant mixture for the toiletry, not only a milder cleansing action, but also certain additional properties, such as, for example, a superfatting effect, an agreeable feeling to the skin during and after the cleansing process, and an improved flow behavior. In addition, it is harmless from the dermatological and toxicological points of view. The $C_8$ to $C_{18}$, preferably $C_{12}$ to $C_{16}$, fatty acid monoester of diglycerol and/or $C_8$ to $C_{18}$, preferably $C_{12}$ to $C_{16}$, fatty acid diester of tetraglycerol can replace an important class of substances for cleansing and/or toilet soaps, the fatty acid alkanolamides, in particular coconut oil fatty acid ethanolamide. These are no longer desired in the cleansing and toilet soaps because, inter alia, they are questionable from a toxicological point of view, since they are suspected of forming nitrosamines.

It is also possible to replace glycerol monolaurate or other fatty acid monoesters of glycerol in the cleansing and toilet soaps. A disadvantageous property of the fatty acid monoesters of glycerol, in particular glycerol monolaurate, is their relatively high melting point (for example 60° C.) and the relatively poor solubility of these compounds, so that the use of fatty acid monoesters of glycerol is only reasonable or suitable in a previously dispersed form.

In a preferred embodiment, the surfactant mixture contains about 2 to 30% by weight of diglycerol monolaurate (relative to the total surfactant content, 100% by weight).

In a preferred embodiment, the washing and cleansing agent and/or toilet soap contains at least one ionic surfactant composed of at least one alkylaryl or alkyl ether-sulfate, hydroxyalkyl ether-sulfonate, alkylsulfate, alkylarylsulfonate, preferably alkylbenzenesulfonate, acylaminopolyglycol ether-sulfate, olefinsulfonate, paraffinsulfonate, sulfosuccinic acid ester and/or fatty alcohol ether-carboxylate and/or, as an amphoteric surfactant, an alkylamidobetaine and/or amphoteric glycerol derivative.

In a further preferred embodiment, the washing agent, cleansing agent and/or toilet soap contains an alkyl ether-sulfate, alkyl ether-sulfonate, hydroxyalkyl ether-sulfonate, aralkyl ether-sulfonate and/or alkylsulfate. The cations present in the surfactants are $Na^+$, $K^+$, $Mg^{++}$, $NH_4^+$, alkylammonium, or alkanolammonium, preferably monoethanolammonium, triethanolammonium, $Na^+$ and/or $NH_4^+$.

In a preferred embodiment, the washing agent, cleansing agent and/or toiletry has a total surfactant content of about 2.5 to 60% by weight, preferably about 7 to 35% by weight (relative to 100% by weight of the agent), and the surfactant mixture contains about 2 to 30% by weight, preferably about 10 to 20% by weight, of at least one fatty acid monoester of diglycerol and/or fatty acid diester of tetraglycerol, relative to the total surfactant content (100% by weight) and about 98 to 70, preferably about 90 to 80, % by weight of at least one ionic surfactant. This ionic surfactant may comprise at least one alkylaryl ether-sulfate or alkyl ether-sulfate, alkylsulfate, alkyl ether-sulfonate, hydroxyalkyl ether-sulfonate, polyhydroxyalkyl ether-sulfonate, alkylarylsulfonate, preferably alkylbenzenesulfonate, acylaminopolyglycol ether-sulfate, olefinsulfonate, paraffinsulfonate, sulfosuccinic acid ester and/or fatty alcohol ether-carboxylate and/or, as an amphoteric surfactant, an alkylamidobetaine and/or an amphoteric glycerol derivative. Preferably the ionic surfactant or surfactant mixture comprises an alkyl ether-sulfate, hydroxyalkyl ether-sulfonate, alkylsulfonate and/or alkylsulfate containing, as the cation, $Na^+$, $K^+$, $Mg^{++}$, $NH_4^+$, monoethanolammonium and/or triethanolammonium, with the residual constituent being solvents and/or diluents, preferably water, lower $C_1$ to $C_8$, preferably $C_2$ to $C_4$, alcohols and/or glycerol or glycerol derivatives, electrolytes and also, if appropriate, additives, preferably preservatives, perfumes, dyes, pharmaceutical active compounds, standardizing agents for regulating the pH, complexing agents for masking metal ions, skin preparations and/or thickeners.

In another preferred embodiment, this agent contains about 7 to 0.1% by weight, preferably about 3 to 0.3% by weight, of at least one electrolyte. The electrolyte is preferably sodium chloride and/or ammonium chloride. The agent preferably contains about 90.5 to 39.9% by weight, preferably about 90 to 64.7% by weight, of a solvent and/or diluent, preferably water, $C_1$ to $C_8$, preferably $C_2$ to $C_4$, lower alcohols and/or $C_3$ to $C_8$, preferably $C_3$ to $C_6$, diols and additives in amounts by weight of about 0.005 to 12 parts by weight, preferably about 0.1 to 5 parts by weight, (relative to 100 parts by weight of the washing agent, cleansing agent and/or toiletry composed of the surfactant mixture, electrolytes and solvent and/or diluent). The agent preferably comprises preservatives, perfumes, dyes, pharmaceutical active compounds, standardizing agents for regulating the pH, complexing agents for masking metal ions, skin preparations and/or thickeners.

It is preferable to employ alkyl ether-sulfates, alkylarylsulfonates, alkylsulfates and alkylsulfonates, esters thereof and olefinsulfonates which have a C number of 8–22, preferably 10–18. In this surfactant, provided with a hydrophobic radical in the form of a saturated, unsaturated or branched hydrocarbon radical, the hydrophobic radical can also be attached via a phenyl radical and/or via other heteroatoms, for example oxygen, to the sulfate and/or sulfonate group, for example as ether ethylsulfates. It is preferable to employ an alkali metal lauryl ether-sulfate, especially sodium lauryl ether-sulfate, an acylaminopolyglycol ether-sulfate, preferably in the form of the alkanolamine compound, especially the triethanolamine salt, a sulfosuccinic acid ester or sulfodicarboxylic acid ester, an alkali metal benzenesulfonate and an ammonium alkylbenzenesulfonate, preferably sodium or ammonium alkylbenzenesulfonate or triethanolammonium alkylbenzenesulfonate and the like.

It is preferable to employ, as alkyl ether-sulfates, compounds of the general formula $RO(C_2H_4O)_nSO_3M$ in which R represents an alkyl chain having 10–18, preferably 12–14, carbon atoms, n represents numbers from 1 to 10 and M represents a cation. These alkyl ether-sulfates are obtained by ethoxylating monohydric alcohols having 10–18 carbon atoms until the desired degree of ethoxylation is achieved and subsequently sulfating and/or neutralizing the product. The neutralization of the acid sulfation products or the sulfonates can be effected by means of alkalis, ammonia, amines or alkanolamines, and/or by means of magnesium hydroxide. It is preferable to employ a hydroxyalkyl ether-sulfonate or polyhydroxyalkyl ether-sulfate which has $C_{10}$–$C_{18}$, preferably $C_{12}$–$C_{14}$, in the fatty acid chain.

In addition to sodium chloride and/or ammonium chloride, the electrolytes used can also be electrolytes which are employed per se in toiletries.

The cleansing agents, washing agents and/or toiletries can also contain other compounds, for example colloids, such as derivatives of cellulose or starch, disinfecting active compounds, fungicidal or antibacterial active compounds, anti-corrosion agents and the like.

The invention also relates to the use of the washing agent, cleansing agent and/or toiletry as a shower gel or shower preparation, bubble bath preparation, liquid hand cleanser or hair shampoo. The agent can be mixed with or dissolved in water prior to contact with the human body, or water can be applied subsequently to assist the cleansing action.

The invention also relates to a process for the preparation of washing agents, cleansing agents and/or toiletries containing at least one ionic and one non-ionic surfactant. The non-ionic surfactant is prepared by reacting fatty acid alkyl esters, monohydroxy-fatty or polyhydroxy-fatty acid alkyl esters having 8–18 C atoms in the fatty acid component and 1–4 C atoms in the ester component in an alkaline medium with one or more isopropylidene derivatives of a polyglycerol. This reaction is carried out with a diglycerol and/or tetraglycerol at temperatures of about 140°–220° C., preferably about 170°–200° C., and in vacuo at 950–5 mbar, preferably at 500–10 mbar, the $C_1$–$C_4$ alcohol thus formed being removed by distillation, preferably continuously. The subsequently purified reaction product, preferably purified by filtration, centrifugation, distillation and/or fractional distillation, is hydrolyzed by splitting off at least one isopropylidene group of the reaction product at about 20°–100° C., preferably about 50° to 80° C., under normal, reduced or elevated pressure by acid hydrolysis. The resulting fatty acid monoesters of diglycerol and/or fatty acid diesters of tetraglycerol are mixed at temperatures of about 1° to 80° C., preferably about 10° to 40° C., and under a pressure or reduced pressure of about 0.1 to 1.5 bar, preferably about 0.3 to 1.2 bar, with at least one ionic surfactant. The ionic surfactant is preferably at least one alkyl ether-sulfate, alkyl ether-sulfonate, hydroxyalkyl ether-sulfonate, polyhydroxyalkyl ether-sulfonate, alkylsulfate, alkylbenzenesulfonate, acylaminopolyglycol ether-sulfate, olefinsulfonate, paraffinsulfonate, sulfosuccinic acid ester, alkylamidobetaine, amphoteric glycine derivative and/or fatty alcohol ether-carboxylate. Other constituents may be added with the surfactant or subsequently.

In the process for the preparation of this non-ionic surfactant, it is preferable to employ an excess of diglycerol for the reaction and/or to separate by distillation a resulting mixture of fatty acid diesters and monoesters of diglycerol.

The pH of the washing agent, cleansing agent and/or toiletry is adjusted to a value of 2–8, preferably 4–7.

The $C_8$ to $C_{18}$, preferably $C_{12}$ to $C_{16}$, fatty acid monoester of diglycerol and/or the $C_8$ to $C_{18}$, preferably $C_{12}$ to $C_{16}$, fatty acid diester of tetraglycerol employed in the surfactant mixture acts as a thickener or agent increasing the viscosity in the washing agent, cleansing agent and/or toiletry. If, for example, an 18% strength by weight solution of sodium lauryl ether-sulfate, i.e., a proportion by weight of 18% by weight of sodium lauryl ether-sulfate in the solution, is used without the concomitant use of other surfactants or additives, but with a content of 1.5% of sodium chloride, a viscosity of 169 mPas results. If 10% by weight of the sodium lauryl ether-sulfate, i.e., 1.8 parts by weight per 100 parts by weight of the solution, are replaced by the same amount by weight, namely 1.8 parts by weight, of diglycerol monolaurate, a viscosity of 1,270 mPas results at a sodium chloride content of 1.5%, or 12,000 mPas at a sodium chloride content of 2% by weight. If 15% by weight of the sodium lauryl ether-sulfate, i.e., 2.7 parts by weight per 100 parts by weight of the solution, are replaced by the same amount by weight of diglycerol monolaurate, a viscosity of 6,200 mPas results at a sodium chloride content of 1.5% by weight.

If 20% by weight of the sodium lauryl ether-sulfate employed (when employing an amount by weight of 18% by weight, that is to say when the amount by weight replaced is 3.6% by weight, or 3.6 parts by weight, relative to 100 parts by weight of the solution) are replaced by the same amount by weight, namely 3.6 parts by weight, of diglycerol monolaurate, a viscosity of 13,000 mPas results at a sodium chloride content of 1.5% by weight.

If, starting from an aqueous solution containing 18% by weight of sodium lauryl ether-sulfate, 10% by weight of the sodium lauryl ether-sulfate employed, that is to say 1.8 parts by weight, are replaced by the same amount by weight of diglycerol monopalmitate, so that the solution prepared contains 16.2% by weight of sodium lauryl ether-sulfate and 1.8% by weight of diglycerol monopalmitate, a viscosity of 704 mPas results at a sodium chloride content of 1.5% by weight and a viscosity of 7,320 mPas results at a sodium chloride content of 9.0% by weight.

If 15% by weight of the sodium lauryl ether-sulfate (relative to an 18% strength by weight solution of sodium lauryl ether-sulfate, that is to say 2.7 parts by weight) are replaced by the same amount by weight of diglycerol monopalmitate, a 15.3% strength by weight solution of sodium lauryl ether-sulfate containing 2.7% by weight of diglycerol monopalmitate is obtained, and a viscosity of 2,250 mPas results at a sodium chloride content of 1.5% by weight.

If the fatty acid monoester of diglycerol and fatty acid diester of tetraglycerol according to the invention are used jointly, it is also possible to improve the foam behavior of the washing agent, cleansing agent and/or toiletry. In practice, a more agreeable, creamy behavior during the shampooing process was also observed in washing tests, when used as a hair shampoo.

In addition, a very good superfatting effect is obtained when the washing agent, cleansing agent and/or toiletry according to the invention is used. The $C_8$ to $C_{18}$, preferably $C_{12}$ to $C_{16}$, fatty acid monoesters of diglycerol and/or $C_8$ to $C_{18}$, preferably $C_{12}$ to $C_{16}$, fatty acid diesters of tetraglycerol employed can, as pure, defined compounds, be prepared free from undesirable by-products and they are included in several countries in the polyglycerol fatty acid ester class of compounds, which are permitted by foodstuffs legislation. These compounds are biodegradable to the extent of over 80% (secondary degradation measured via decrease in chemical oxygen demand).

The fatty acid monoesters of diglycerol and/or fatty acid diesters of tetraglycerol employed have a lard-like consistency and can therefore be incorporated easily and are readily or clearly soluble in the customary surfactant concentrations.

EXAMPLES

1. Hair shampoo standard formulations (total surfactant content approx. 18% by weight)

| | |
|---|---|
| Sodium lauryl ether-sulfate, 70% strength | 21.9% by wt. |
| Diglycerol monolaurate | 2.7% by wt. |
| Sodium chloride | 1.5% by wt. |
| Preservative | 0.05% by wt. |
| Perfume | 0.2% by wt. |
| Water, completely freed from salts | 73.65% by wt. |

Viscosity: 6,200 mPas.
Ross/Miles foam numbers, DIN 53,902. 1 g/l of detergent substance, 40° C., distilled $H_2O$: 163/155.
Foam behavior:
This was measured by the Ross/Miles method in a 1 g/l solution of active substance in distilled $H_2O$ at 40° C. The following foam values were found: with the addition of fatty acid monoester of diglycerol as described under 1.

| height of foam | |
|---|---|
| immediately | 163 mm |
| after 5 seconds | 155 mm |

(Average values) compared with 18% strength sodium lauryl ether-sulfate (detergent substance, that is to say total surfactant content) without addition.

| height of foam | |
|---|---|
| immediately | 139 mm |
| after 5 seconds | 130 mm |

This means an average increase of 17% in foam volume as a result of the use of fatty acid monoesters of diglycerol.

2. Hair shampoo standard formulations (total surfactant content approx. 18% by weight)

| | |
|---|---|
| Sodium lauryl ether-sulfate, 70% strength | 21.9% by wt. |
| Diglycerol monolaurate | 2.7% by wt. |
| Sodium chloride | 1.5% by wt. |
| Preservative | 0.05% by wt. |
| Perfume | 0.2% by wt. |
| Water, completely freed from salts | 73.65% by wt. |

Viscosity: 11,000 mPas.
Ross/Miles foam numbers, DIN 53,902.
1 g/l of detergent substance, 40° C., distilled $H_2O$: 165/158.
Viscosity measured at 20° C. by a VT 181 rotational viscometer made by Haake.

3. Formulation for a toiletry kind to the skin and a hair shampoo kind to the skin (approx. 22% total surfactant content)

| | |
|---|---|
| Sodium lauryl ether-sulfate, 70% strength | 13.0% by wt. |
| Disodium fatty alcohol polyglycol ether-sulfosuccinate, 40% strength (sulfosuccinic acid ester) | 25.5% by wt. |
| Diglycerol monolaurate | 2.7% by wt. |
| Sodium chloride | 4.0% by wt. |
| Water, completely freed from salts | 54.8% by wt. |

Viscosity: 2,300 mPas.
Ross/Miles foam numbers, DIN 53,902.
1 g/l of detergent substance, 40° C., distilled $H_2O$: 165/156.

4. Formulation for a toiletry kind to the skin and a hair shampoo kind to the skin (approx. 16% total surfactant content)

| | |
|---|---|
| Sodium lauryl ether-sulfate, 70% strength | 11.1% by wt. |
| Triethanolamine acylaminopolyglycol ether-sulfate, 40% strength | 10.0% by wt. |
| Fatty acid amidoethyl-2-hydroxyethyl-carboxymethylammonium laurylsulfate (amphoteric glycine derivative), 38% strength | 8.0% by wt. |
| Digylcerol monolaurate | 2.0% by wt. |
| Sodium chloride | 1.7% by wt. |
| Perfume | 0.3% by wt. |
| Preservative | 0.05% by wt. |
| Lactic acid | 0.1% by wt. |
| Water, completely freed from salts | 66.75% by wt. |

Viscosity: 3,000 mPas.
Ross/Miles foam numbers, DIN 53,902.
1 g/l of detergent substance, 40° C., distilled $H_2O$: 184/172.

5. Toiletry and toilet detergent formulation without sodium lauryl ether-sulfate (having approx. 20% total surfactant content)

| | |
|---|---|
| Amphoteric glycine derivative, 38% strength (see Example 4) | 20% by wt. |
| Sulfosuccinic acid ester, 40% strength (see Example 3) | 20% by wt. |
| Diglycerol monolaurate | 5% by wt. |
| Ammonium chloride | 0.5% by wt. |
| Water, completely freed from salts | 54.4% by wt. |

Viscosity: 2.450 mPas.
Ross/Miles foam numbers, DIN 53,902.
1 g/l of detergent substance, 40° C., distilled H$_2$O: 180/171.

6. Mild hair shampoo (having approx. 17% by weight total surfactant content)

| | |
|---|---|
| Sodium lauryl ether-sulfate, 70% strength | 14% by wt. |
| Triethanolamine acylaminopolyglycol ether-sulfate, 40% strength | 10% by wt. |
| Amphoteric glycine derivative (see Example 4), 38% strength | 6.3% by wt. |
| Tetraglycerol diisostearate | 1.5% by wt. |
| Sodium chloride | 2.5% by wt. |
| Perfume | 0.3% by wt. |
| Preservative | 0.05% by wt. |
| Water, completely freed from salts | 65.35% by wt. |

Viscosity: 1,800 mPas.
Ross/Miles foam numbers, DIN 53,902.
1 g/l of detergent substance, 40° C., distilled H$_2$O: 135/125.

7. Washing-up agent (having approx. 20% total surfactant content)

| | |
|---|---|
| Sodium alkylbenzenesulfonate, 50% strength | 23.8% by wt. |
| Sodiumlauryl ether-sulfate, 70% strength | 7.3% by wt. |
| Diglycerol monolaurate | 3.0% by wt. |
| Perfume | 0.15% by wt. |
| Preservative | 0.05% by wt. |
| Water, completely freed from salts | 65.7% by wt. |

Viscosity: 1,300 mPas.
Ross/Miles foam numbers, DIN 53,902.
1 g/l of detergent substance, 40° C., distilled H$_2$O: 201/189.

8. Car shampoo (having approx. 20% total surfactant content)

| | |
|---|---|
| Triethanolammonium alkylbenzenesulfonate, 50% strength | 25% by wt. |
| Sodiumlauryl ether-sulfate, 70% strength | 8% by wt. |
| Diglycerol monolaurate | 2% by wt. |
| Sodium chloride | 1% by wt. |
| Perfume | 0.15% by wt. |
| Preservative | 0.05% by wt. |
| Water, completely freed from salt | 63.8% by wt. |

Viscosity: 2,400 mPas.
Ross/Miles foam numbers, DIN 53,902.
1 g/l of detergent substance, 40° C., distilled H$_2$O: 161/151.

What is claimed is:

1. A dermatologically and toxicologically safe washing agent, cleansing agent or toiletry, comprising, in admixture:
   (1) from 2.5 to 60% by weight of surfactant comprising:
      (a) from 2 to 30% by weight, based on total surfactant content, of at least one non-ionic fatty acid ester surfactant selected from the group consisting of a C$_8$ to C$_{18}$ fatty acid monoester of diglycerol and a C$_8$ to C$_{18}$ fatty acid diester of tetraglycerol, and
      (b) at least one anionic surfactant selected from the group consisting of alkylethersulfate, alkylsulfate, alkylarylsulfonate, acylaminopoly-glycol ether-sulfate, olefinsulfonate, paraffin-sulfonate, sulfosuccinic acid ester and fatty alcohol ether carboxylate or at least one amphoteric surfactant selected from the group consisting of an alkylamidobetaine and an amphoteric glycerol derivative;
   the balance of the mixture comprising:
   (2) a solvent, and
   (3) optionally one or more additives selected from the group consisting of electrolytes, preservatives, perfumes, dyes, pharmaceutically-active compounds, standardizing agents for regulating pH, complexing agents for masking metal ions, skin preparations, thickeners, disinfectants, antibacterial agents, and anti-corrosion agents.

2. An agent as claimed in claim 1, wherein the mixture comprises from 10 to 20% by weight of said fatty acid ester, relative to the total surfactant content.

3. An agent as claimed in claim 1, additionally comprising at least one electrolyte in an amount by weight of 0.1 to 8% by weight, relative to the total weight of the agent.

4. An agent as claimed in claim 3, wherein the electrolyte is an inorganic chloride present in an amount of 0.7 to 3% by weight.

5. An agent as claimed in claim 1, wherein the total surfactant content of the mixture is 7 to 35% by weight.

6. An agent as claimed in claim 1, wherein the solvent comprises at least one member selected from the group consisting of water, lower C$_1$ to C$_8$ alcohols, C$_2$ to C$_8$ diols, glycerol and glycerol derivatives.

7. An agent as claimed in claim 1, wherein the solvent comprises at least one member selected from the group consisting of water, C$_2$ to C$_4$ alcohols, C$_3$ to C$_6$ diols, glycerol and glycerol derivatives.

8. An agent as claimed in claim 1, comprising at least one additive selected from the group consisting of preservatives, perfumes, dyes, pharmaceutically-active compounds, standardizing agents for regulating the pH, complexing agents for masking metal ions, skin preparations and thickeners.

9. An agent as claimed in claim 1, comprising from 2.5 to 60% by weight of total surfactant, wherein from 2 to 30% by weight of the total surfactant comprises the fatty acid ester.

10. An agent as claimed in claim 9, comprising from 7 to 0.1% by weight of at least one electrolyte, from 90.5 to 39.9% by weight of a solvent, and from 0.005 to 12 parts by weight of at least one additive, in each case relative to the total weight of the mixture.

11. An agent as claimed in claim 1, comprising from 7 to 35% by weight of total surfactant, wherein from 10 to 20% by weight of the total surfactant comprises the fatty acid ester.

12. An agent as claimd in claim 11, comprising from 3 to 0.3% by weight of at least one electrolyte, from 90 to 64.7% by weight of a solvent, and from 0.1 to 5 parts by weight of at least one additive, in each case relative to the total weight of the mixture.

13. An agent as claimed in claim 9, wherein the solvent comprises at least one member selected from the group consisting of water, lower C$_1$ to C$_8$ alcohols, C$_2$ to C$_8$ diols, glycerol and glycerol derivatives.

14. An agent as claimed in claim 9, wherein the solvent comprises at least one member selected from the group consisting of water, $C_2$ to $C_4$ alcohols, $C_3$ to $C_6$ diols, glycerol and glycerol derivatives.

15. An agent as claimed in claim 1, wherein the fatty acid ester comprises diglycerol monolaurate.

16. An agent as claimed in claim 1, wherein the ionic surfactant contains $Na^+$, $K^+$, $Mg^{++}$, $NH_4^+$, alkylammonium or alkanolammonium as the cation.

17. An agent as claimed in claim 1, wherein the cation is monoethanolammonium, triethanolammonium, $Na^+$ or $NH_4^+$.

18. An agent as claimed in claim 9, wherein said ionic or amphoteric surfactant comprises from 98 to 70% by weight of the mixture.

19. An agent as claimed in claim 9, wherein said ionic or amphoteric surfactant comprises from 90 to 80% by weight of the mixture.

20. An agent as claimed in claim 18, wherein said ionic surfactant is selected the group consisting of alkylaryl ether sulfate, alkyl ether sulfate, alkylsulfate, alkyl ether sulfonate, hydroxyalkyl ether sulfonate, polyhydroxyalkyl ether sulfonate, alkylarylsulfonate, acylamino polyglycol ether sulfate, olefinsulfonate, paraffinsulfonate, sulfosuccinic acid ester, fatty alcohol ether carboxylate, and said amphoteric surfactant is selected from the group consisitng of an alkylamido betaine and an amphoteric glycerol derivative.

21. An agent as claimed in claim 20, wherein said ionic or amphoteric surfactant comprises an alkyl ether sulfate, hydroxyalkyl ether sulfonate, alkylsulfonate or alkylsulfate having $Na^+$, $K^+$, $Mg^{++}$, $NH_4^+$, monoethanolammonium or triethanolammonium as the cation.

22. A method of cleaning the human body, comprising the steps of:
   providing an agent as claimed in claim 1, and
   applying the agent to a portion of the human body to cleanse the body.

23. An agent as claimed in claim 1, comprising, in admixture:
   (1) from 2.5 to 60% by weight of surfactant consisting essentially of;
      (a) from 2 to 30% by weight, based on total surfactant content, of at last one non-ionic fatty acid ester surfactant selected from the group consisting of a $C_8$ to $C_{18}$ fatty acid monoester of diglycerol and a $C_8$ to $C_{18}$ fatty acid diester of tetraglycerol, and
      (b) at least one dermatologically and toxicologically safe ionic surfactant selected from the group consisting of alkylethersulfate, alkylsulfate, alkylarylsulfonate, acylaminopolyglycol ether-sulfate, olefinsulfonate, paraffin-sulfonate, sulfosuccinic acid ester and fatty alcohol ether carboxylate or amphoteric surfactant selected from the group consisting of an alkylamidobetaine and an amphoteric glycerol derivative;
   the balance of the mixture comprising:
   (2) a solvent, and
   (3) optionally one or more additives selected from the group consisting of electrolytes, preservatives, perfumes, dyes, pharmaceutically-active compounds, standardizing agents for regulating pH, complexing agents for masking metal ions, skin preparations and thickeners.

24. An agent as claimed in claim 2, wherein the total surfactant content of the mixture is 7 to 35% by weight.

* * * * *